(12) United States Patent
Lee et al.

(10) Patent No.: US 8,865,093 B2
(45) Date of Patent: Oct. 21, 2014

(54) POLYMORPH, POLYMORPH SCREENING SYSTEM, AND POLYMORPH PREPARING AND SCREENING METHOD

(75) Inventors: Tu Lee, Flushing, NY (US); Shih-Chia Chang, Pingjhen (TW); Jen-Fan Peng, Zhunan Township (TW); Pu-Yun Wang, Fengshan (TW); Yu-Kun Lin, Banqiao (TW)

(73) Assignee: National Central University, Jhongli (TW)

( * ) Notice: Subject to any disclaimer, the term of this patent is extended or adjusted under 35 U.S.C. 154(b) by 578 days.

(21) Appl. No.: 13/277,446

(22) Filed: Oct. 20, 2011

(65) Prior Publication Data

US 2012/0035064 A1 Feb. 9, 2012

Related U.S. Application Data (63) Continuation of application No. 12/586,892, filed on Sep. 29, 2009.

(30) Foreign Application Priority Data

May 26, 2009 (TW) ................................ 98117559 A (51) Int. Cl.
*B01J 8/00* (2006.01)
*C40B 60/08* (2006.01)
*B01J 19/00* (2006.01)
*G01N 33/15* (2006.01)

(52) U.S. Cl.
CPC .... *B01J 19/0046* (2013.01); *B01J 2219/00637* (2013.01); *C40B 60/08* (2013.01); *B01J 2219/00495* (2013.01); *B01J 2219/00702* (2013.01); *B01J 2219/0072* (2013.01); *B01J 2219/00756* (2013.01); *B01J 2219/00585* (2013.01); *G01N 33/15* (2013.01); *B01J 2219/00617* (2013.01); *B01J 2219/00621* (2013.01); *B01J 2219/00612* (2013.01); *B01J 2219/00533* (2013.01); *B01J 2219/0061* (2013.01)
USPC .......................................... 422/608; 435/6.11

(58) Field of Classification Search
CPC .................... B01J 19/0046; B01J 2219/00274
USPC .......................................... 506/17; 435/6.11
See application file for complete search history.

(56) References Cited

U.S. PATENT DOCUMENTS

2006/0213425 A1* 9/2006 Myerson et al. ................. 117/68

* cited by examiner

*Primary Examiner* — Natalia Levkovich
(74) *Attorney, Agent, or Firm* — Hudak, Shunk & Farine Co. LPA (57) ABSTRACT

A polymorph, a polymorph screening system, and a polymorph preparing and screening method are disclosed. The polymorph preparing and screening method includes the following steps: providing a plurality of substrates of different materials; causing an organic material to grow crystals on the plurality of substrates through solution-cooling crystallization process, so that a plurality of polymorphs with different characteristics are prepared; and screening the plurality of polymorphs prepared in the previous step to obtain polymorphs with desired characteristics.

6 Claims, 8 Drawing Sheets

POLYMORPH, POLYMORPH SCREENING SYSTEM, AND POLYMORPH PREPARING AND SCREENING METHOD

CROSS REFERENCE

This is a division of U.S. application Ser. No. 12/586,892, filed Sep. 29, 2009 for POLYMORPH, POLYMORPH SCREENING SYSTEM, AND POLYMORPH PREPARING AND SCREENING METHOD, which claims priority to Taiwanese Patent Application No. 098117559 filed May 26, 2009.

FIELD OF THE INVENTION

The present invention relates to a polymorph, a polymorph screening system, and a polymorph preparing and screening method; and more particularly to polymorph screening method that enable quick screening of a plurality of polymorphs to obtain desired ones therefrom.

BACKGROUND OF THE INVENTION

When molecules, atoms and ions accurately self-assemble into different forms in a solid and continuously repeat such forms in a long space, such pattern of self-assembly is referred to as "polymorph". Different polymorphs have unique physical and chemical characteristics, including melting point, density, crystal morphology, solubility, and mechanical property.

In a method currently adopted by pharmaceutical industry to find suitable medicament, a slide with a protein film attached thereto is used as a substrate. Since this type of substrate has a special organic functional group formed thereon, it can be used to locate expecting medicament. According to some literatures, through evaporation coating, it is able to cause an organic material to form a monolayer on a substrate. In this case, the substrate is a semiconductor wafer having different crystallographic faces, bringing the molecules of the organic material to arrange in different orientations. In the conventional ways of finding polymorphs, different solvents are used to dissolve the organic material to prepare a mother liquor, and various crystallization processes, such as solution-cooling crystallization, anti-solvent crystallization or evaporative crystallization, can be used to prepare polymorphs from the mother liquor. However, according to the conventional crystallization processes, after the crystallization, steps such as filtering the mother liquor and drying are needed to thereby take more time to produce the polymorphs, and the prepared polymorphs could not be analyzed sooner to obtain the desired polymorphs. In brief, the conventional polymorph preparing and screening process is time-consuming and cost-waste.

SUMMARY OF THE INVENTION

A primary object of the present invention is to provide a polymorph preparing and screening method, so as to increase the efficiency in preparing and screening polymorphs and accordingly, largely reduce the time and cost thereof, and to find new material characteristics from polymorphs.

To achieve the above and other objects, the polymorph preparing and screening method according to the present invention includes the following steps: (1) providing a plurality of substrates of different materials, and these substrate can be disposed on the same base plate, for example, in a chip-base array; (2) causing an organic material to grow crystals on the plurality of substrates through solution-cooling crystallization process, so that a plurality of polymorphs with different characteristics are prepared; and (3) analyzing the plurality of polymorphs prepared in the step (2) using a characteristic analyzing unit and screening the prepared polymorphs to obtain the polymorphs with desired characteristics. In the solution-cooling crystallization, the organic material is dissolved in a solvent in a high-temperature environment of about 60-100° C., so as to form a high-temperature saturated solution. The high-temperature saturated solution is then dripped on the different substrates and accordingly cools from the high temperature to room temperature. Under the effect of supersaturation and of solvent volatilization, a drive for self-assembly is formed on the surfaces of the molecules and the substrates to thereby induce polymorphs. The substrates can be a semiconductor wafer substrate, a polymeric substrate, a thin-film substrate, a glass substrate and a plastic substrate. The organic material is a semiconductor material and/on a biomedical material. The characteristic analyzing unit is selected from the group consisting of a DSC, an OM, an FT-IR, an XRD, and any combination thereof, so as to examine the crystallized solids and determine the possible types of the prepared polymorphs.

The present invention also provides a polymorph that is prepared using the above-described polymorph preparing and screening method.

The polymorph preparing and screening method provided by the present invention provide at least one or more of the following advantages:

(1) The present invention employs crystallization engineering and technology for an organic material to crystallize on different substrates through solution-cooling crystallization process, so as to exploit different polymorphs, from which some polymorphs with desired characteristics are screened out. The method of the present invention is efficient and can be widely applied to different industrial manufacturing processes to reduce the time and cost therefor.

(2) By combining the crystallization engineering and technology with organic substrate array for use in the exploitation of new polymorphs, it is able to quickly and conveniently find the polymorphs of a certain organic material and understand the influences of the organic self-assembly monolayer on polymorphs. In addition, to increase the applicability of polymorphs, multiple substrates of different materials are disposed on the same base plate in a chip-based array. By doing this, new polymorphs can be exploited, and the potential applicability of the polymorphs can be analyzed and discovered using a characteristic analyzing unit to thereby provide a material with new characteristics.

(3) From the present invention it is found, due to the microscale thereof, the organic material is affected by the functional groups on the substrates or by the orientation of the atoms or molecules of the substrates to thereby have changes in their molecular packing and molecular organization, which results in the forming of polymorphs that often have unique physical and chemical characteristics. Therefore, the present invention can be conveniently applied to quickly develop new material properties without the need of changing the molecular composition of the organic material.

(4) By using different organic interfaces, that is, the substrates of different material, to induce polymorphs of the solid crystals of a solute (i.e. the organic material), the purpose of efficient polymorph screening can be achieved.

(5) In the method of the present invention, the high-temperature-saturated solution is dripped on the substrates, so that the organic material re-crystallizes on the substrates due to solution cooling and solvent volatilization. Since the steps of filtering the mother liquor and drying after the crystallization in the conventional crystallization process are omitted in the present invention, the polymorphs can be prepared with shortened time and be presented for analyzing more quickly.

(6) In the present invention, the crystallization occurs on a base plate having a plurality of substrates of different material disposed thereon, enabling the polymorphs prepared on the substrates to be analyzed at one time to largely increase the polymorph screening speed. The present invention can be applied to various industrial fields, such as food industry, medical industry, photoelectric industry, semiconductor industry, agriculture, and ceramic industry. With the fast polymorph preparing and screening method of the present invention, different polymorphs of different substances can be discovered and a user can screen out the polymorphs with desired characteristics for use.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

The present invention will now be described with some preferred embodiments thereof. For the purpose of easy to understand, elements that are the same in these preferred embodiments are denoted by the same reference numerals.

Figure 1:
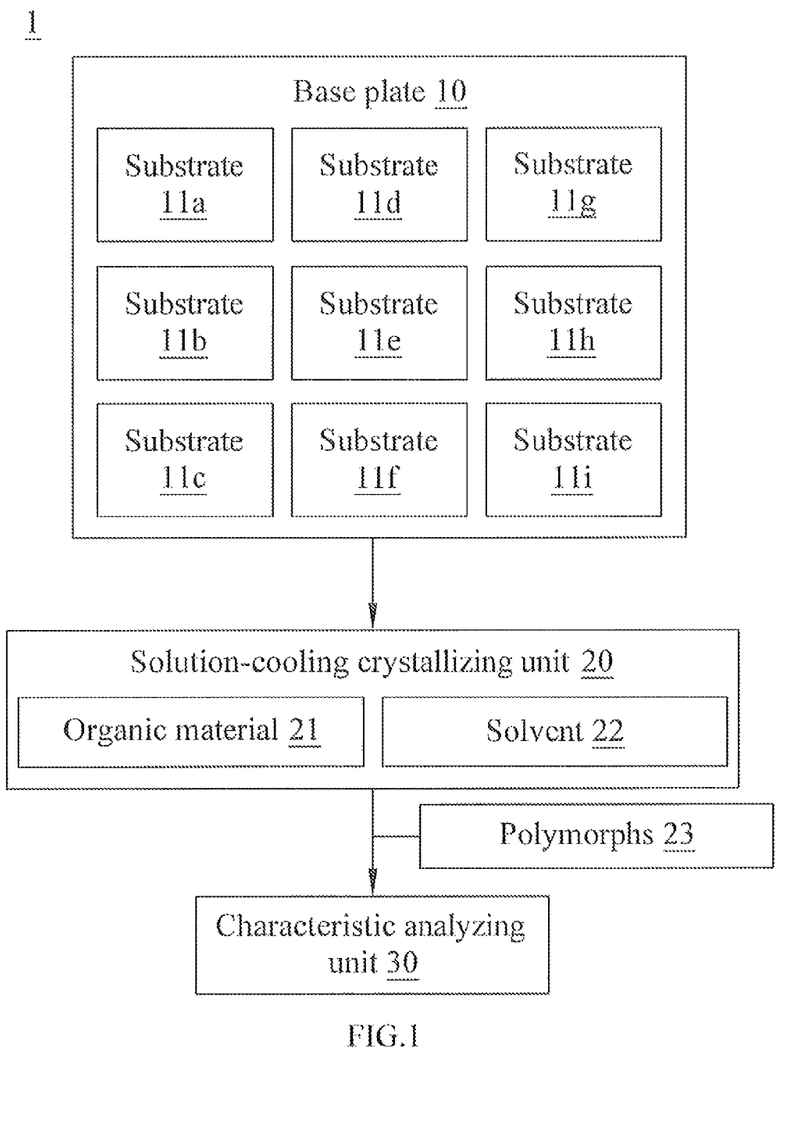
FIG. 1 is a block diagram of a polymorph screening system according to an embodiment of the present invention.

Please refer to FIG. 1 that is a block diagram of a polymorph screening system 1 according to an embodiment of the present invention. As shown, the polymorph screening system 1 can include a base plate 10, a solution-cooling crystallizing unit 20, and a characteristic analyzing unit 30. On the base plate 10, there is a plurality of substrates 11a-11i of different materials, such as a semiconductor substrate, a polymeric substrate, a thin-film substrate, a glass substrate, and a plastic substrate having different crystallographic faces. The solution-cooling crystallizing unit 20 can be used to perform solution-cooling crystallization, so that an organic material 21 is dissolved in a solvent 22 under a high-temperature environment of 60-100° C. to produce a high-temperature saturated solution. Then, the high-temperature saturated solution is applied to the plurality of substrates 11a-11i to cool from a high temperature to about room temperature. Under the effect of supersaturation and of the solvent volatilization, crystals grow on the substrates 11a-11i and a plurality of different polymorphs 23 are prepared. The characteristic analyzing unit 30 can be used to screen the plurality of polymorphs 23, so as to obtain the polymorphs with desired characteristics. Preferably, the substrates 11a-11i can be disposed on the base plate 10 in a chip-based array. The organic material 21 can include a small-molecular organic material, which can be, for example, a semiconductor material, a biomedical material and the like. The characteristic analyzing unit 30 can include a differential scanning calorimeter (DSC), an optical microscope (OM), a Fourier transform infrared spectroscope (FT-IR), and/or an X-ray diffractometer (XRD).

Figure 2:
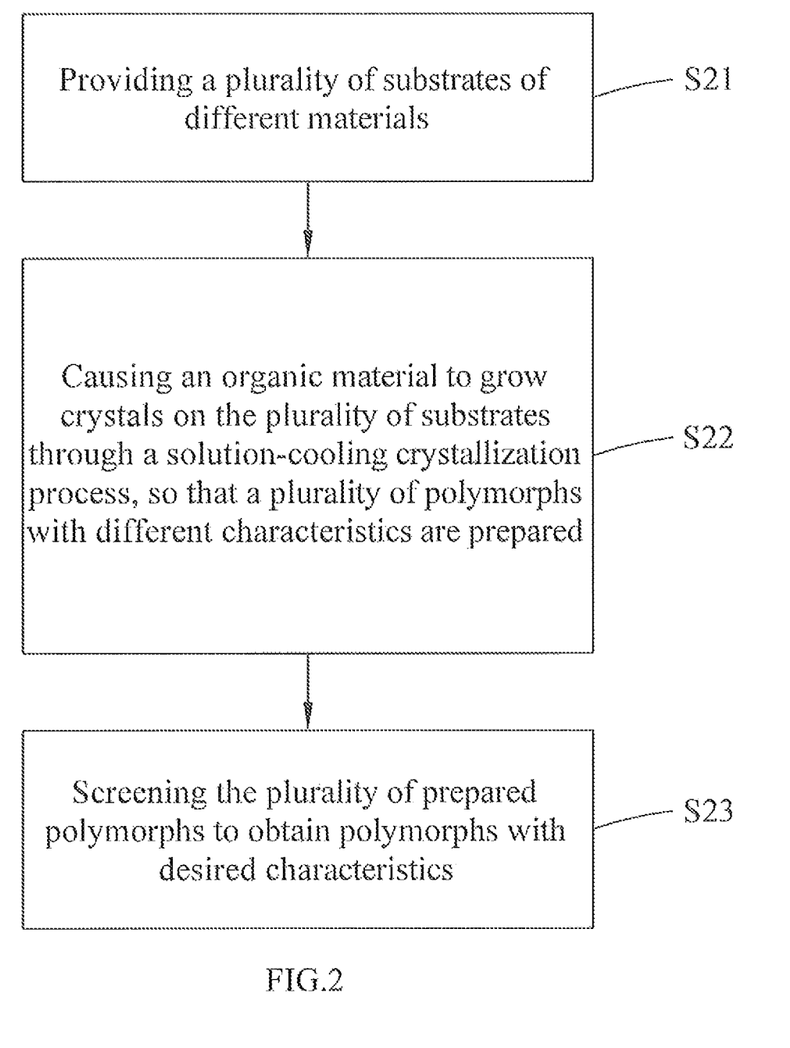
FIG. 2 is a flowchart showing the steps included in a polymorph preparing and screening method according to the present invention.

Please refer to FIG. 2 that is a flowchart showing the steps included in a polymorph preparing and screening method according to the present invention. As shown, in a first step S21, a plurality of substrates of different materials are provided. In a second step S22, the solution-cooling crystallization process is employed for an organic material to grow crystals on the plurality of substrates, so that a plurality of polymorphs with different characteristics are prepared. And, in a third step S23, the plurality of polymorphs prepared in the step S22 are screened to obtain polymorphs with desired characteristics. In the above-described method, the plurality of substrates are disposed on the same base plate in a chip-based array, for example. The substrates can include a semiconductor substrate, a polymeric substrate, a thin-film substrate, a glass substrate, and a plastic substrate having different crystallographic faces. The organic material can include a small-molecular organic material, which can be, for example, a semiconductor material, a biomedical material and the like. Further, a characteristic analyzing unit, such as a differential scanning calorimeter (DSC), an optical microscope (OM), a Fourier transform infrared spectroscope (FT-IR) or an X-ray diffractometer (XRD), can be used to examine the crystallized solids and further determine the possible types of polymorphs, so as to screen the crystallized solids and obtain the polymorphs with the desired characteristics.

Figure 3:
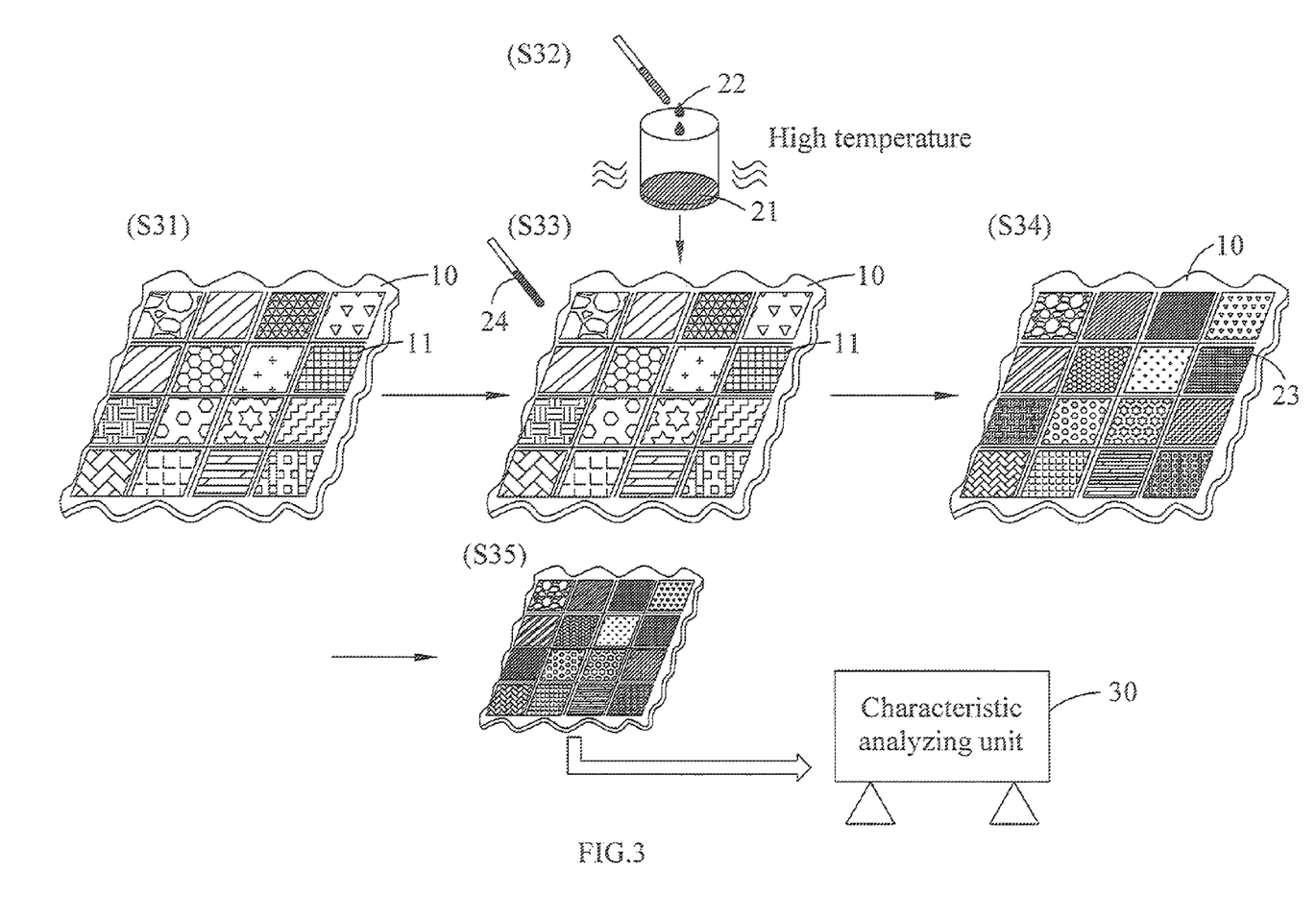
FIG. 3 illustrates a polymorph preparing and screening method according to an embodiment of the present invention.

Please refer to FIG. 3, in which a polymorph preparing and screening method according to a first embodiment of the present invention is illustrated. As shown, in a first step S31 of this method, a plurality of substrates 11 of different materials are provided and disposed on the same base plate 10. In a second step S32, an organic material 21 is disposed in a high-temperature environment and a solvent 22 is slowly added to the organic material 21, so that the organic material 21 is dissolved to produce a high temperature saturated solution 24. In a third step S33, the high-temperature saturated solution 24 is quickly applied to the plurality of substrates 11. In a fourth step S34, the base plate 10 with the plurality of substrates 11 disposed thereon is positioned under room temperature, allowing the solvent 22 to evaporate gradually. With the evaporation of the solvent 22, the organic material 21 gradually crystallizes on the plurality of substrates 11 to form a plurality of polymorphs 23 having different physical or chemical characteristics. And, in a fifth step S35, the base plate 10 with the plurality of polymorphs 23 is positioned in a characteristic analyzing unit 30 for screening, so that polymorphs with desired characteristics are obtained. In the first embodiment of the method of the present invention, since the substrates 11, the organic material 21 and the characteristic analyzing unit 30 selected for use are similar to those described above, they are not repeatedly discussed herein.

Figure 4:
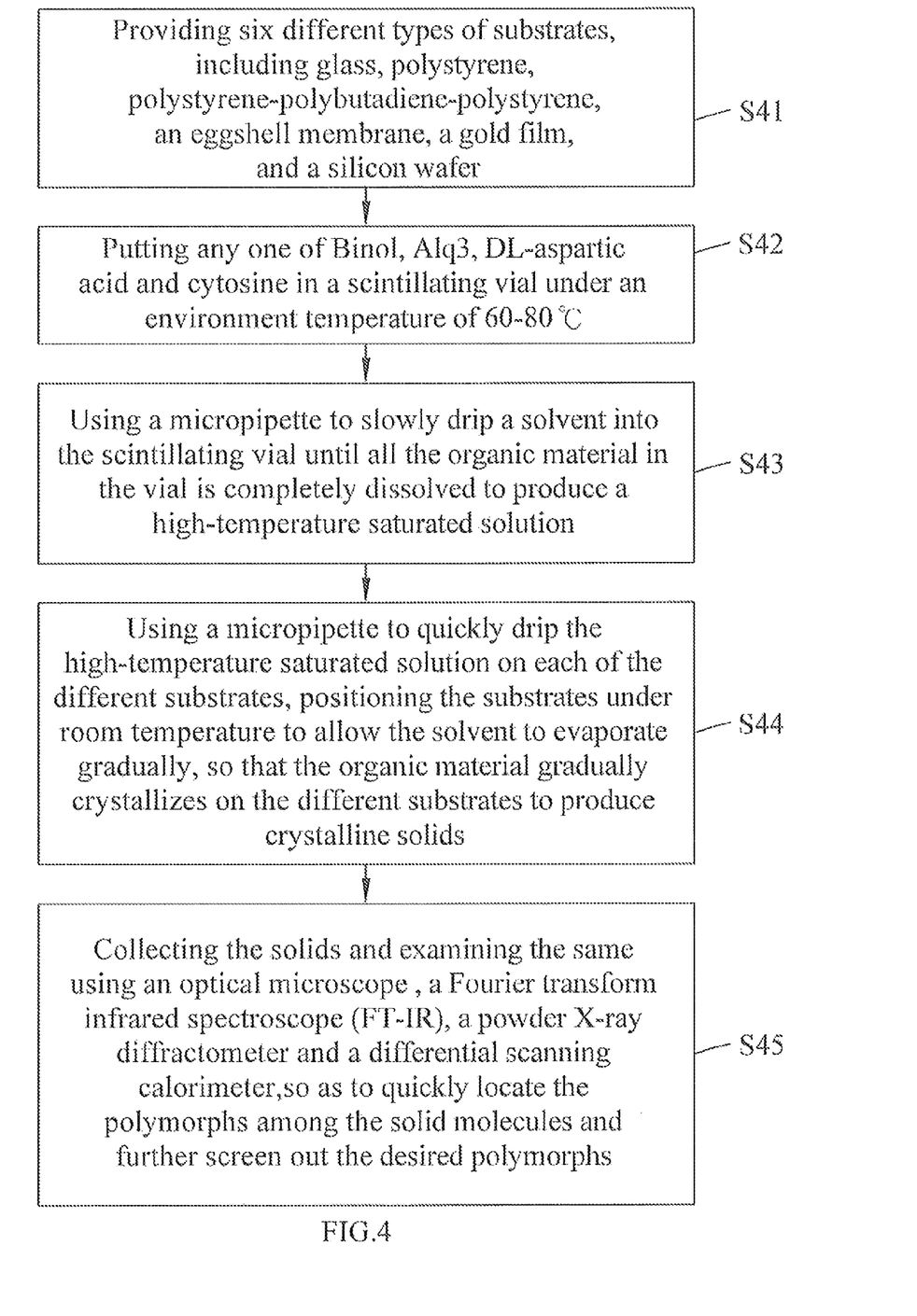
FIG. 4 is a flowchart showing the steps included in a polymorph preparing and screening method according to another embodiment of the present invention.
Figure 5A:
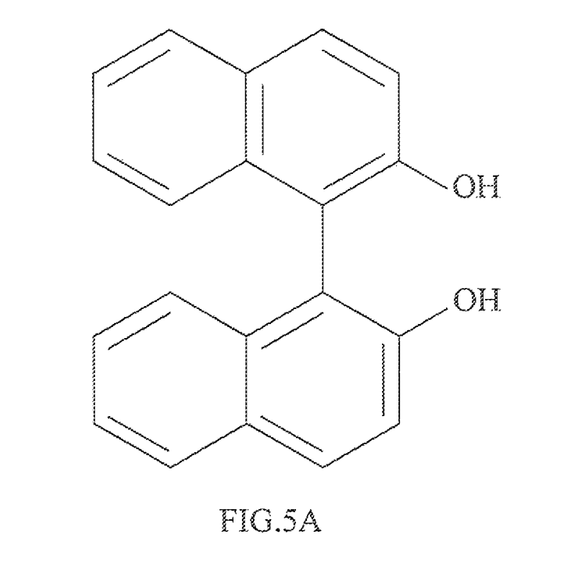
FIGS. 5A to 5D are structural formulas of Binol, Alq3, DL-aspartic acid, and cytosine, respectively, which are used as organic materials in the polymorph preparing and screening method of the present invention.
Figure 5B:
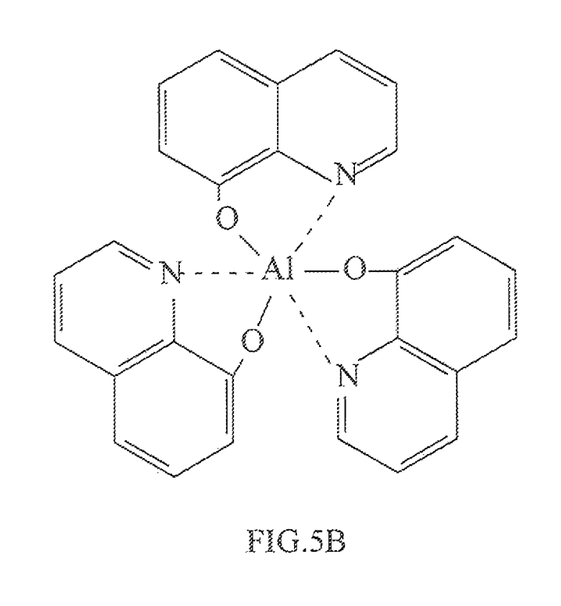
Figure 5C:
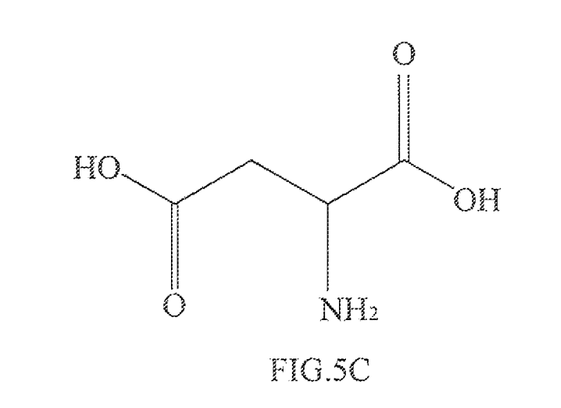
Figure 5D:
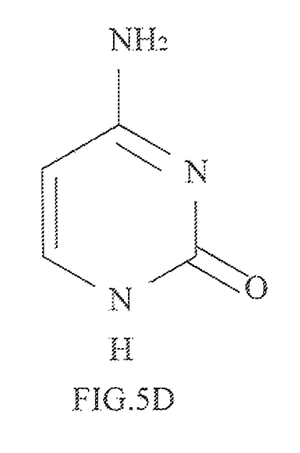

FIG. 4 is a flowchart showing the steps included in a polymorph preparing and screening method according to a second embodiment of the present invention. As shown, in a first step S41 for the second embodiment, six different types of substrates are provided, including glass, polystyrene (PS), polystyrene-polybutadiene-polystyrene (PS-PB-PS), an eggshell membrane, a gold film, and a silicon wafer. In a second step S42, about 10-100 mg of an organic material, which can be any one of 1,1-Bi-2-naphthol (i.e. Binol), tris-(8-hydroxyquinoline) aluminum (III) (i.e. Alq3), DL-aspartic acid and cytosine, the structural formulas of which are illustrated in FIGS. 5A, 5B, 5C and 5D, respectively, is put in a 10-20 ml scintillating vial; and the scintillating vial is indirectly heated in a water tank to keep the environment temperature at 60-80° C. In a third step S43, a solvent is slowly dripped into the scintillating vial using a 20-200 μL micropipette until all the organic material in the vial is completely dissolved to produce a high-temperature saturated solution. In a fourth step S44, a 20-200 μL micropipette is used to quickly drip the high-temperature saturated solution on each of the different substrates, and the substrates are positioned under room temperature, allowing the solvent to evaporate gradually. With the cooling of the high-temperature saturated solution and the evaporation of the solvent, the solute gradually crystallizes on the different substrates to produce crystalline solids. Finally, in a fifth step S45, the solids are collected and observed using an optical microscope (OM), so as to determine whether these solids are different in crystal morphology. In addition, an FT-IR, a powder X-ray diffractometer (PXRD), and a DSC are used to examine the crystalline solids, in order to quickly locate the polymorphs among the solid molecules and further screen out the desired polymorphs.

According to the method shown in FIG. 4, Binol, Alq3, DL-aspartic acid and cytosine are separately caused to grow crystals on each of the glass substrate, the PS substrate, the PS-PB-PS substrate, the eggshell membrane substrate, the gold film substrate and the silicon wafer substrate through the solution-cooling crystallization process. Since the high-temperature saturated solution on the substrates is in contact with air of room temperature on a sudden, the temperature of the solution lowers quickly and the solvent evaporates in the environment. At this point, temperature drop and evaporation form two drives for crystallization, bringing the solute to quickly nucleate and grow crystals on the substrates. After a period of time, the substrates are observed with an OM and examined with DSC, FT-IR and PXRD. It is found the polymorphs prepared on different substrates have different characteristics in terms of their solubility, crystal morphology, melting point, hardness, etc., and the observation results are shown in Tables 1, 2, 3 and 4. As can be found from the results, due to the micro-scale thereof, the small molecules of Binol, Alq3, DL-aspartic acid and cytosine are affected by the functional groups on the substrates or the orientation of the atomic or molecular arrangement of the substrates to thereby have changes in their molecular packing and molecular organization, which results in the forming of polymorphs, which often have unique physical and chemical characteristics. Therefore, the method of the present invention can be conveniently applied to quickly develop new material properties without the Peed of changing the molecular composition of the organic material.

TABLE 1

Crystallization of Binol on Different Substrates

| Sample | DCS onset temperature (° C.) | Crystal morphology under OM |
|---|---|---|
| Re-crystallized Binol On glass | 198, 211 | Thin film without distinct crystal shape |
| Re-crystallized Binol on PS | 198, 212 | Rectangular tube |
| Re-crystallized Binol on PS-PB-PS | 197, 212 | Round column |
| Re-crystallized Binol on eggshell membrane | 214 | Column |

TABLE 1-continued

Crystallization of Binol on Different Substrates

| Sample | DCS onset temperature (° C.) | Crystal morphology under OM |
|---|---|---|
| Re-crystallized Binol on silicon wafer | 198, 211 | Round sheet |
| Re-crystallized Binol on gold film | 216 | Column |

TABLE 2

Crystallization of AlQ3 on Different Substrates

| Sample | Image under OM | IR Spectrum | PXRD Pattern |
|---|---|---|---|
| Re-crystallized AlQ3 On glass | Square plate | — | — |
| Re-crystallized AlQ3 on PS | Needle | As usual | As usual |
| Re-crystallized AlQ3 on PS-PB-PS | Column | As usual | As usual |
| Re-crystallized AlQ3 on eggshell membrane | Square plate | Strength reduced, position of absorption peak changed | $2\theta = 8.43°, 14.8°, 17.1°, 18.7°, 20.3°, 27.7°, 31.0°$, changes existed |
| Re-crystallized AlQ3 on silicon wafer | Rectangular plate | As usual | $2\theta = 8.43°, 17.1°, 20.3°, 27.7°$, changes existed |
| Re-crystallized AlQ3 on gold film | Rectangular plate | As usual | $2\theta = 8.43°, 12.2°, 17.1°, 20.3°$, changes existed |

TABLE 3

Crystallization of DL-Aspartic Acid on Different Substrates

| Sample | DCS onset temperature (° C.) | Crystal morphology under OM |
|---|---|---|
| Re-crystallized DL-Aspartic Acid on glass | 218 | Long column |
| Re-crystallized DL-Aspartic Acid on PS | 214 | Long column |
| Re-crystallized DL-Aspartic Acid on PS-PB-PS | 214 | Long column |
| Re-crystallized DL-Aspartic Acid on eggshell membrane | 218 | Long column |
| Re-crystallized DL-Aspartic Acid on silicon wafer | 218 | Long column |
| Re-crystallized DL-Aspartic Acid on gold film | 220 | Long column |

TABLE 4

Crystallization of Cytosine on Different Substrates

| Sample | DCS onset temperature (° C.) | Crystal morphology under OM |
|---|---|---|
| Re-crystallized Cytosine On glass | 83 | Flat sheet |
| Re-crystallized Cytosine on PS | 87 | Flat sheet |
| Re-crystallized Cytosine on PS-PB-PS | Heat absorption does not occur until 300° C. | Flat sheet |
| Re-crystallized Cytosine on eggshell membrane | 97, 203 | Feather-like piece |
| Re-crystallized Cytosine on silicon wafer | 90 | Flat sheet |

TABLE 4-continued

Crystallization of Cytosine on Different Substrates

| Sample | DCS onset temperature (° C.) | Crystal morphology under OM |
|---|---|---|
| Re-crystallized Cytosine on gold film | Heat absorption does not occur until 300° C. | Flat sheet |

The present invention has been described with some preferred embodiments thereof and it is understood that many changes and modifications in the described embodiments can be carried out without departing from the scope and the spirit of the invention that is intended to be limited only by the appended claims.

What is claimed is:

1. A polymorph preparing and screening method, comprising the following steps:
   providing a plurality of substrates each made of different materials;
   disposing an organic material in a environment with temperature about 60-100° C., and continuously adding a solvent slowly into the organic material in order to dissolve the organic material, so as to produce a high-temperature saturated solution;
   applying the high-temperature saturated solution to the plurality of substrates and then disposing the plurality of substrates under room temperature to cool down the high-temperature saturated solution on the plurality of substrates, and then allowing the solvent to volatilize to make the organic material crystallize on the plurality of substrates each made of different materials, thereby forming a plurality of polymorphs having different characteristics; and
   using a characteristic analyzing unit comprising a differential scanning calorimeter, an optical microscope, a Fourier transform infrared spectroscope, or a X-ray diffractometer to screen the plurality of polymorphs to obtain polymorphs with a desired characteristic;
   wherein the plurality of substrates are selected from the group consisting of a semiconductor wafer substrate, a polymeric substrate, and a plastic substrate;
   wherein the plurality of substrates each made of different materials are disposed on a same base plate.

2. The polymorph preparing and screening method as claimed in claim 1, wherein the plurality of substrates are disposed on the same base plate in a way of a chip-based array.

3. The polymorph preparing and screening method as claimed in claim 1, wherein the plurality of substrates are selected from the group consisting of polystyrene, polystyrene-polybutadiene-polystyrene, an eggshell membrane, a gold film, and a silicon wafer.

4. The polymorph preparing and screening method as claimed in claim 1, wherein the organic material is selected from the group consisting of a semiconductor material and a biomedical material.

5. The polymorph preparing and screening method as claimed in claim 4, wherein the semiconductor material is selected from the group consisting of 1,1-Bi-2-naphthol and tris-(8-hydroxyquinoline) aluminum (III).

6. The polymorph preparing and screening method as claimed in claim 4, wherein the biomedical material is selected from the group consisting of DL-aspartic acid and cytosine.

* * * * *